United States Patent [19]

Moore et al.

[11] Patent Number: 5,332,860
[45] Date of Patent: Jul. 26, 1994

[54] POLYOLS USEFUL FOR PREPARING POLYURETHANE FOAMS HAVING IMPROVED RETENTION OF INSULATIVE PROPERTIES, POLYURETHANE FOAMS PREPARED THEREWITH AND METHODS FOR THE PREPARATION THEREOF

[75] Inventors: Douglas R. Moore, Clute; Warren A. Kaplan, Lake Jackson; Ricky L. Tabor, Lake Jackson; Alan K. Schrock, Lake Jackson, all of Tex.

[73] Assignee: The Dow Chemical Company, Midland, Mich.

[21] Appl. No.: 85,331

[22] Filed: Jun. 29, 1993

[51] Int. Cl.$^5$ ............... C07C 69/03; C07C 69/76; C07C 69/82

[52] U.S. Cl. ............................ 560/91; 521/172; 560/198

[58] Field of Search .............. 560/91, 198; 521/172

[56] References Cited

U.S. PATENT DOCUMENTS

| | | |
|---|---|---|
| 1,714,173 | 5/1929 | Kessler et al. |
| 3,647,759 | 3/1972 | Walker. |
| 4,039,487 | 8/1977 | Kolakowski et al. ............ 521/159 |
| 4,048,104 | 9/1977 | Svoboda et al. .................. 521/159 |
| 4,092,276 | 5/1978 | Narayan ............................ 521/108 |
| 4,223,068 | 9/1980 | Carlstrom et al. ................ 428/310 |
| 4,237,238 | 12/1980 | DeGuiseppi et al. ............. 521/131 |
| 4,246,364 | 1/1981 | Koehler et al. ................... 521/167 |
| 4,246,365 | 1/1981 | Wiedermann et al. ........... 521/172 |
| 4,307,205 | 12/1981 | Bershas ............................ 521/171 |
| 4,336,341 | 6/1982 | Fujiwara et al. .................. 521/109 |
| 4,469,824 | 9/1984 | Grigsby, Jr. et al. .............. 521/173 |
| 4,481,309 | 11/1984 | Straehle et al. ................... 521/172 |
| 4,487,853 | 12/1984 | Reichel et al. .................... 521/172 |
| 4,521,611 | 6/1985 | Magnus ............................ 560/91 |
| 4,526,908 | 7/1985 | Magnus et al. ................... 521/172 |
| 4,529,744 | 7/1985 | Wood ................................ 521/131 |
| 4,530,938 | 7/1985 | White ............................... 521/105 |
| 4,542,163 | 9/1985 | White et al. ...................... 521/105 |
| 4,544,679 | 10/1985 | Tideswell et al. ................ 521/116 |

(List continued on next page.)

OTHER PUBLICATIONS

German Abstract 1,555,908.
BE Abstract-771815-Q.
Chemical Abstract 89: 110981r.
Chemical Abstract 77764h.
German Abstract 2,110,278.
DT Abstract-210278-Q.
Chemical Abstract 125522u.
Chemical Abstract 26048r.
Derwent Abstract 85-052388/09.

*Primary Examiner*—John Kight, III
*Assistant Examiner*—Shelley A. Dodson

[57] ABSTRACT

Polyurethane foams having improved retention of insulative properties can be prepared using one or more of two novel polyols. One of the polyols is a polyether prepared by reacting a monoepoxide with a compound having the general formula:

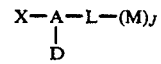

wherein X is H, Li, Na, K; A is N, S or O; L is a covalent bond or a connecting group having from 1 to 10 carbons; M is any group capable of reacting with an ethylene oxide molecule in the presence of a basic catalyst; and J is an integer from 2 to 8. The other polyol is prepared by (1) admixing ethylene carbonate and one or more hydroxyl functional compounds under reaction conditions sufficient to react the ethylene carbonate and the hydroxyl functional compounds to produce a polyol precursor, and (2) admixing the polyol precursor with diethylene glycol and an anhydride, a dicarboxylic acid, a tricarboxylic acid or mixtures thereof, optionally in the presence of a catalyst.

4 Claims, No Drawings

U.S. PATENT DOCUMENTS

| | | | |
|---|---|---|---|
| 4,582,926 | 4/1986 | Straehle et al. | 560/91 |
| 4,595,711 | 6/1986 | Wood | 521/158 |
| 4,604,410 | 8/1986 | Altenberg | 521/172 |
| 4,605,729 | 8/1986 | Barnes et al. | 528/301 |
| 4,615,822 | 10/1986 | Magnus | 252/182 |
| 4,642,319 | 2/1987 | McDaniel | 521/175 |
| 4,644,019 | 2/1987 | McDaniel | 521/173 |
| 4,644,027 | 2/1987 | Magnus et al. | 524/375 |
| 4,644,047 | 2/1987 | Wood | 528/176 |
| 4,644,048 | 2/1987 | Magnus et al. | 528/176 |
| 4,647,595 | 3/1987 | Kozawa et al. | 521/158 |
| 4,654,377 | 3/1987 | Molring et al. | 560/198 |
| 4,691,045 | 9/1987 | Fukuchi et al. | 560/185 |
| 4,753,967 | 6/1988 | Londrigan | 521/172 |
| 4,845,266 | 7/1989 | Mark et al. | 560/91 |
| 4,859,791 | 8/1989 | Nodelman et al. | 560/91 |
| 4,902,816 | 2/1990 | McDaniel | 560/91 |
| 5,001,165 | 3/1991 | Canaday et al. | 521/131 |
| 5,003,027 | 3/1991 | Nodelman | 528/79 |
| 5,114,755 | 5/1992 | Canaday et al. | 427/373 |

POLYOLS USEFUL FOR PREPARING POLYURETHANE FOAMS HAVING IMPROVED RETENTION OF INSULATIVE PROPERTIES, POLYURETHANE FOAMS PREPARED THEREWITH AND METHODS FOR THE PREPARATION THEREOF

BACKGROUND OF THE INVENTION

The present invention relates to polyols useful for preparing polyurethane foams having improved retention of insulative properties, polyurethane foams prepared therewith and methods for the preparation there of.

It is known to prepare polyurethanes by reacting polyisocyanates with active hydrogen containing materials. For example, it is known to combine methylene diphenyldiisocyanate (MDI) or polymeric methylene diphenyldiisocyanate (PMDI) with polyether or polyester polyols to prepare polyurethane foams having good insulative properties. These insulating foams may be found in applications ranging from home construction to ice chests and refrigerators and even to industrial applications such as pipe and vessel insulation.

In addition to good insulative properties, polyurethane foams, particularly rigid polyurethane foams can have other desirable properties. For example, such foams can have good structural properties such as compressive strength, abrasion resistance and dimensional stability upon exposure to temperature and humidity changes. Isocyanurate foams can have particularly good flame resistance. All of these properties are resultant upon a careful choice of formulation components used to prepare the foams.

But preparing polyurethane foams is not always trouble free. Sometimes problems can arise with formulations which do not have some desired physical property. For example, a foam can have poor flame resistance and a reformulation to correct that problem may be required. Other problems can arise in other areas not directly associated with foam properties. For example, the use of chlorofluorocarbon (CFC) blowing agents has become subject to increasing criticism and regulation due to environmental concerns.

One solution to the use of CFC blowing agents in preparing polyurethane foams has been to use alternative blowing agents such as carbon dioxide and hydrochlorofluorcarbon (HCFC) blowing agents. But such a solution can sometimes be a problem in itself. Use of carbon dioxide and HCFC blowing agents can result in polyurethane foams which can lose some of their insulative properties over time. It would be desirable in the art of preparing polyurethane foams with alternative blowing agents to prepare foams which can retain their insulative properties longer than conventional foams.

SUMMARY OF THE INVENTION

In one aspect the present invention is a polyol useful for preparing a polyurethane foam having improved retention of insulative properties comprising compounds having the general formula:

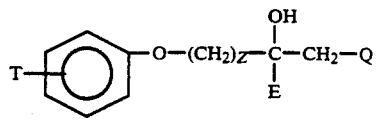

wherein T is any group substantially unreactive with epichlorohydrin except a halogen, E is H, an alkyl group, or a hydroxy substituted alkyl group, Z is an integer from 0 to 8 and Q has the general formula:

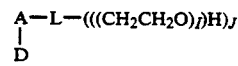

wherein A is N, S or O; L is a covalent bond or a connecting group having from 1 to 10 carbons and optionally having OH groups; I is an integer from 1 to 10; J is an integer from 2 to 8; and D is H, L-$(((CH_2CH_2O)_I)H)_J$, an alkyl or an aromatic group if A is N or an electron pair if A is S or O.

In another aspect, the present invention is a method of preparing a polyol having the general formula:

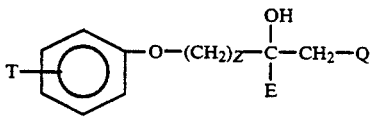

wherein T is any group substantially unreactive with epichlorohydrin except a halogen, E is H, an alkyl group, or a hydroxy substituted alkyl group, Z is an integer from 0 to 8 and Q has the general formula:

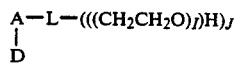

wherein A is N, S or O; L is a covalent bond or a connecting group having from 1 to 10 carbons and optionally having OH groups; I is an integer from 1 to 10; J is an integer from 2 to 8; and D is H, L-$(((CH_2CH_2O)_I)H)_J$, an alkyl or an aromatic group if A is N or an electron pair if A is S or O; comprising the steps of (1) preparing a polyol initiator by reacting compounds having the general formula:

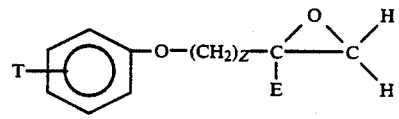

and

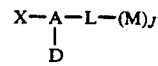

wherein T, E, Z, A, L, D and J are as defined above; X is H, Li, Na, K; and M is any group capable of reacting with an ethylene oxide molecule in the presence of a basic catalyst; and (2) reacting the initiator of Step 1 with ethylene oxide in the presence of a basic catalyst under reaction conditions sufficient to form a polyol.

Yet another aspect of the present invention is a polyester polyol useful for preparing polyurethane foams having improved retention of insulative properties comprising the product of (1) admixing ethylene carbonate and one or more hydroxyl functional compounds under reaction conditions sufficient to react the ethylene carbonate and the hydroxyl functional compounds to produce a polyol precursor, and (2) admixing the polyol precursor with diethylene glycol and an anhydride, a dicarboxylic acid, a tricarboxylic acid or mixtures thereof, optionally in the presence of a catalyst, under reaction conditions sufficient to prepare a polyester polyol.

Another aspect of the present invention is a method of preparing a polyester polyol useful for preparing polyurethane foams having improved retention of insulative properties comprising the steps of (1) admixing ethylene carbonate and one or more hydroxyl functional compounds under reaction conditions sufficient to react the ethylene carbonate and the hydroxyl functional compounds to produce a polyol precursor, and (2) admixing the polyol precursor with diethylene glycol and an anhydride, a dicarboxylic acid, a tricarboxylic acid or mixtures thereof, optionally in the presence of a catalyst, under reaction conditions sufficient to prepare a polyester polyol.

In still another aspect, the present invention is a polyurethane foam having improved retention of insulative properties comprising the reaction product of admixing a polyurethane formulation including (I) a polyisocyanate, (II) an active hydrogen containing material selected from the group consisting of:
(A) compounds having the general formula:

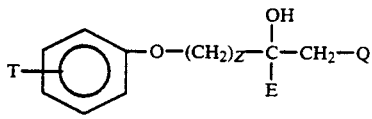

wherein T is any group substantially unreactive with epichlorohydrin except a halogen, E is H, an alkyl group, or a hydroxy substituted alkyl group, Z is an integer from 0 to 8 and Q has the general formula:

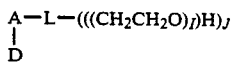

wherein A is N, S or O; L is a covalent bond or a connecting group having from 1 to 10 carbons and optionally having OH groups; I is an integer from 1 to 10; J is an integer from 2 to 8; and D is H, L-$(((CH_2CH_2O)_I)H)_J$, an alkyl or an aromatic group if A is N or an electron pair if A is S or O; (B) polyester polyols which are the product of (1) admixing ethylene carbonate and one or more hydroxyl functional compounds under reaction conditions sufficient to react the ethylene carbonate and the hydroxyl functional compounds to produce a polyol precursor, and (2) admixing the polyol precursor with diethylene glycol and an anhydride, a dicarboxylic acid, a tricarboxylic acid or mixtures thereof, optionally in the presence of a catalyst, under reaction conditions sufficient to prepare a polyester polyol; and (C) mixtures thereof, and (III) a carbon dioxide blowing agent, optionally in the presence of a catalyst, under reaction conditions sufficient to prepare a polyurethane foam.

In another aspect, the present invention is a method of preparing a polyurethane foam having improved retention of insulative properties comprising admixing a polyurethane formulation including (I) a polyisocyanate, (II) an active hydrogen containing material selected from the group consisting of:
(A) compounds having the general formula:

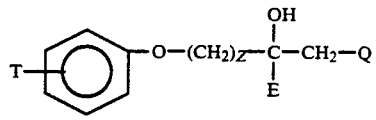

wherein T is any group substantially unreactive with epichlorohydrin except a halogen, E is H, an alkyl group, or a hydroxy substituted alkyl group, Z is an integer from 0 to 8 and Q has the general formula:

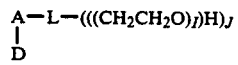

wherein A is N, S or O; L is a covalent bond or a connecting group having from 1 to 10 carbons and optionally having OH groups; I is an integer from 1 to 10; J is an integer from 2 to 8; and D is H, L-$(((CH_2CH_2O)_I)H)_J$, an alkyl or an aromatic group if A is N or an electron pair if A is S or O; (B) polyester polyols which are the product of (1) admixing ethylene carbonate and one or more hydroxyl functional compounds under reaction conditions sufficient to react the ethylene carbonate and the hydroxyl functional compounds to produce a polyol precursor, and (2) admixing the polyol precursor with an anhydride, a dicarboxylic acid, a tricarboxylic acid or mixtures thereof, optionally in the presence of a catalyst, under reaction conditions sufficient to prepare a polyester polyol; and (C) mixtures thereof, and (III) a carbon dioxide blowing agent, optionally in the presence of a catalyst, under reaction conditions sufficient to prepare a polyurethane foam.

In still another aspect, the present invention is a polyurethane formulation useful for preparing a polyurethane foam having improved retention of insulative properties comprising: (I) a polyisocyanate, (II) an active hydrogen containing material selected from the group consisting of:
(A) compounds having the general formula:

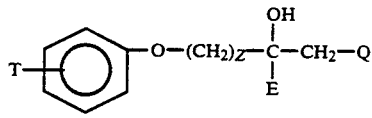

wherein T is any group substantially unreactive with epichlorohydrin except a halogen, E is H, an alkyl group, or a hydroxy substituted alkyl group, Z is an integer from 0 to 8 and Q has the general formula:

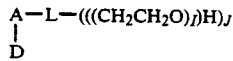

wherein A is N, S or O; L is a covalent bond or a connecting group having from 1 to 10 carbons and optionally having OH groups; I is an integer from 1 to 10; J is an integer from 2 to 8; and D is H, L-$(((CH_2CH_2O)_I)H)_J$, an alkyl or an aromatic group if A is N or an electron pair if A is S or O; (B) polyester polyols which are the product of (1) admixing ethylene carbonate and one or more hydroxyl functional compounds under reaction conditions sufficient to react the ethylene carbonate and the hydroxyl functional compounds to produce a polyol precursor, and (2) admixing the polyol precursor with diethylene glycol and an anhydride, a dicarboxylic acid, a tricarboxylic acid or mixtures thereof, optionally in the presence of a catalyst, under reaction conditions sufficient to prepare a polyester polyol; and (C) mixtures thereof, (III) a carbon dioxide blowing agent, and optionally, (IV) a catalyst.

DESCRIPTION OF THE PREFERRED EMBODIMENTS

In one embodiment, the present invention is a polyurethane foam having improved retention of insulative properties. The use of non-CFC blowing agents, (hereinafter alternative blowing agents) can result in a phenomena wherein a foam, freshly prepared from a polyurethane formulation including an alternative blowing agent, can have good insulative properties, but then lose those good properties more quickly than a foam prepared from an otherwise similar polyurethane foam formulation including CFC blowing agents. It is believed that this results from a tendency of alternative blowing agents to more readily permeate out of polyurethane foam while air permeates into the foam. It is known that air has poorer insulative properties (resulting in foam with higher k-factor) than carbon dioxide and other alternative blowing agents such as HCFCs. The foams of the present invention can resist the permeation of carbon dioxide better than conventional foams. The foams of the present invention can retain their insulative properties longer than conventional foams.

In one embodiment, the present invention is a polyurethane foam having improved retention of insulative properties comprising the reaction product of admixing a polyisocyanate, a carbon dioxide blowing agent and an active hydrogen containing material including compounds having the general formula:

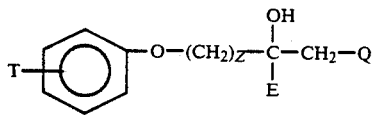

wherein T is any group substantially unreactive with epichlorohydrin except a halogen, E is H, an alkyl group, or a hydroxy substituted alkyl group, Z is an integer from 0 to 8 and Q has the general formula:

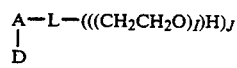

wherein A is N, S or O; L is a covalent bond or a connecting group having from 1 to 10 carbons and optionally having OH groups; I is an integer from 1 to 10; J is an integer from 2 to 8; and D is H, L-(((CH$_2$CH$_2$O)$_I$)H)$_J$, an alkyl or an aromatic group if A is N or an electron pair if A is S or O. These active hydrogen containing materials can be polyols prepared with initiators prepared from a monofunctional epoxy resin and a dialkanolnucleophile or a polynucleophile. The method of preparing these materials includes the steps of (1) preparing a polyol initiator by reacting compounds having the general formula:

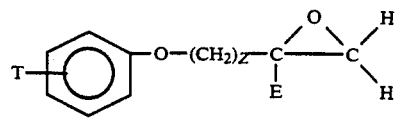

and

wherein T, E, Z, A, L, D and J are as defined above; X is H, Li, Na, K; and M is any group capable of reacting with an ethylene oxide molecule in the presence of a basic catalyst; and (2) reacting the initiator of Step 1 with ethylene oxide in the presence of a basic catalyst under reaction conditions sufficient to form a polyol.

These polyols include those prepared with initiators which are the reaction product of admixing a monofunctional epoxy resin with a dialkanolamine under reaction conditions sufficient to prepare an initiator. For example, one such initiator is prepared by admixing a cresyl glycidyl ether and diethanolamine. Other monofunctional epoxy resins which can be used with the present invention include but are not limited to phenyl glycidyl ether, dimethyl benzyl glycidyl ether, hydroxyacetanilide glycidyl ether, hydroxyphenylacetanilide glycidyl ether and the like.

The dialkanolnucleophiles useful for preparing the polyol initiators of the present invention are preferably alkanolamines such as diethanolamine, dipropanolamine, N,N-diethanol ethylenediamine and the like. However polynucleophiles can also be used to prepare the initiators useful for preparing the polyols of the present invention. Any compound having the general formula:

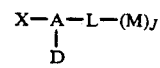

wherein A is N, S or O, L is a covalent bond or a connecting group having from 1 to 10 carbons; D is H, L-(((CH$_2$CH$_2$O)$_I$)H)$_J$ an alkyl or an aromatic group if A is N or an electron pair if A is S or O; J is an integer from 2 to 8; X is H, Li, Na, or K; and M is any group capable of reacting with an ethylene oxide molecule in the presence of a basic catalyst. This group of compounds includes but is not limited to diethanol mercaptan, 2,2-diethanol-potassium ethoxide, hydroxyethyl piperazine, aniline ethanolamine, ethylene diamine and the like.

Any compound which according to above general formula can be used to prepare the present invention. For example, one such compound has the structure:

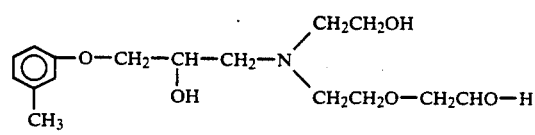

and is preferred. Another preferred compound has the structure:

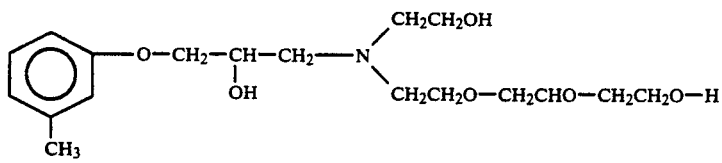

The monofunctional epoxy compounds and dialkanolnucleophile and/or polynucleophile useful for preparing the polyols of the present invention are admixed under reaction conditions sufficient to prepare a polyol initiator. The conditions used can be any which will result in the product initiators described above. Preferably, the reaction conditions are admixing the monofunctional epoxy and dialkanolnucleophile and/or polynucleophile compounds slowly at about 25° to about 150° C., preferably at about 50° to about 125° C. and most preferably about 100° C. and then raising the temperature of the admixed reactants to from 80° to about 150° C., preferably from about 100° to about 110° C. for about two hours.

The initiators, once prepared can be reacted with ethylene oxide and propylene oxide, preferably only ethylene oxide to prepare a polyether polyol. Preparing a polyether polyol by reacting ethylene or propylene oxide with a hydroxy functional initiator is well known in the art. However, the polyols of the present invention are generally prepared by reacting the initiator with the epoxide in the presence of a basic catalyst such as sodium or potassium hydroxide and tertiary amines. The resultant polyols have a secondary and/or tertiary hydroxyl on the polymer backbone. The secondary and/or tertiary hydroxyl containing polyols of the present invention have an equivalent weight of from about 60 to about 200, preferably from about 70 to about 150, and more preferably from about 75 to about 125. They have a nominal functionality of about 3 to about 9, preferably from about 3 to about 7 and most preferably from about 3 to about 5.

In another embodiment, the present invention is polyurethane foam having improved retention of insulative properties comprising the reaction product of admixing a polyisocyanate, a carbon dioxide blowing agent and an active hydrogen containing material which is a polyester polyol. The polyester polyol is prepared by (1) admixing ethylene carbonate and one or more hydroxyl functional compounds under reaction conditions sufficient to react the ethylene carbonate and the hydroxyl functional compounds to produce a polyol precursor, and (2) admixing the polyol precursor with diethylene glycol and an anhydride, a dicarboxylic acid, a tricarboxylic acid or mixtures thereof, optionally in the presence of a catalyst, under reaction conditions sufficient to prepare a polyester polyol.

The polyol precursor can be prepared with any hydroxyl functional compound having minimum nominal functionality of 2 and a maximum functionality of 12 and having from 2 to 24 carbon atoms. Sugars or sugar derivatives are typical compounds of this type and are preferred, but other compounds such as glycerine and trimethylolpropane can also be used. Sugars and sugar derivatives useful with the present invention include but are not limited to pentaerythritol, xylitol, arabitol, sorbitol, mannitol, fructose, sucrose, α-methyl glucoside, β-methyl glucoside and the like. Preferably, the sugar or sugar derivative is sorbitol or a mixture of sugars with sorbitol being present at greater than 50 percent by weight of the sugar and sugar derivative mixture. Such polyols are often lower in viscosity than conventional polyols which can ease handling difficulties in preparing polyurethane foams.

The hydroxyl functional compounds and ethylene carbonate are admixed under conditions sufficient to react the ethylene carbonate and hydroxyl functional compounds to produce a polyol precursor. The progress of this reaction can be monitored directly using an infrared (IR) spectrometer. Ethylene carbonate has a strong carbonyl absorption peak at 1795 cm$^{-1}$. As the reaction proceeds to completion, this peak will decrease in intensity. The length time required to complete the reaction will vary with the temperature and hydroxyl functional compounds used, as well as other reaction variables, but, generally, the hydroxyl functional compounds and ethylene carbonate are reacted for from about 4 hours to about 18 hours at from about 100 to about 200° C., preferably for from about 6 to about 12 hours at from about 120° to about 180° C., and more preferably for from about 7 to about 12 hours at from about 140° to 160° C.

The polyol precursor is next reacted with diethylene glycol, and an anhydride, a dicarboxylic acid, a tricarboxylic acid or mixture thereof, optionally in the presence of a catalyst. Compounds which can be used include but are not limited to: fumaric acid, tetrahydro phthalic acid, glutaric acid, pyromellitic acid, maleic acid and the like. One preferred material is phthalic anhydride. Another is dimethyl terephthalate. Dimethyl isophthalate, dimethyl terephthalate bottoms from dimethyl terephthalate production, and even recycled polyethylene terephthalate can be used with the present invention as long as the material used is an anhydride, a dicarboxylic acid, a tricarboxylic acid or mixture thereof. A catalyst to accelerate the reaction of the components can also be used. For example catalysts such as dibutyl tin dilaurate, stannous octoate, stannous oleate, stannous acetate, stannous laurate, manganese acetate, zinc acetate, potassium acetate, sodium acetate and the like can be used with the present invention.

The reaction of the polyol precursor, diethylene glycol and an anhydride, a dicarboxylic acid, a tricarboxylic acid or mixtures thereof can be monitored by observing hydroxy number or acid number changes. Preferably, the acid number will be less than 5 mg KOH/g polyol. The reactants are reacted at from about 130° to about 280° C., preferably from about 150° to about 250° C. and more preferably from about 175° to about 240° C. The polyester polyols of the present invention have at least one secondary or tertiary hydroxyl on the polymer backbone.

The formulations of the present invention can include minor amounts of active hydrogen containing materials other than those discussed above. Active hydrogen containing compounds most commonly used in polyurethane production are those compounds having at least two hydroxyl groups. Those compounds are referred to herein as polyols. Representatives of suitable polyols are generally known and are described in such publications as *High Polymers*, Vol. XVI, "Polyurethanes, Chemistry and Technology" by Saunders and Frisch, Interscience Publishers, New York, Vol. I, pp. 32–42, 44–54 (1962) and Vol. II, pp. 5–6, 198–199 (1964); *Organic Polymer Chemistry* by K. J. Saunders, Chapman and Hall, London, pp. 323–325 (1973); and *Developments in Polyurethanes*, Vol. I, J. M. Burst, ed., Applied Science Publishers, pp. 1–76 (1978). However, any active hydrogen containing compound can be used with the method of this invention. Examples of such materials include those selected from the following classes of compositions, alone or in admixture: (a) alkylene oxide adducts of polyhydroxyalkanes; (b) alkylene oxide adducts of sugars and sugar derivatives; (c) alkylene oxide adducts of phosphorus and polyphosphorus acids; and (d) alkylene oxide adducts of polyphenols. Polyols of these types are referred to herein as "base polyols". Examples of alkylene oxide adducts of polyhydroxyalkanes useful herein are adducts of ethylene glycol, propylene glycol, 1,3-dihydroxypropane, 1,4-dihydroxybutane, and 1,6-dihydroxyhexane, glycerol, 1,2,4-trihydroxybutane, 1,2,6-trihydroxyhexane, 1,1,1-trimethylolethane, 1,1,1-trimethylolpropane, pentaerythritol, polycaprolactone, xylitol, arabitol, sorbitol, mannitol, and the like. Preferred herein as alkylene oxide adducts of polyhydroxyalkanes are the ethylene oxide adducts of trihydroxyalkanes. Other useful adducts include ethylene diamine, glycerin, ammonia, 1,2,3,4-tetrahydroxy butane, fructose, and sucrose.

Also preferred are poly(oxypropylene) glycols, triols, tetrols and hexols and any of these that are capped with ethylene oxide. These polyols also include poly(oxypropyleneoxyethylene)polyols. The oxyethylene content should preferably comprise less than about 80 weight percent of the total and more preferably less than about 40 weight percent. The ethylene oxide, when used, can be incorporated in any way along the polymer chain, for example, as internal blocks, terminal blocks, or randomly distributed blocks, or any combination thereof.

The base polyols described hereinabove can contain small amounts of "inherent" unsaturation, i.e., unsaturation due to the isomerization of propylene oxide to allyl alcohol during the manufacture of the polyol. In some cases it may be desirable to include additional unsaturation in the polyols.

Polyamines, amine-terminated polyols, polymercaptans and other isocyanate-reactive compounds are also suitable in the present invention. Polyisocyanate polyaddition active hydrogen containing compounds (PIPA) are particularly preferred for use with the present invention. PIPA compounds are typically the reaction products of TDI and triethanolamine. A method for preparing PIPA compounds can be found in, for example, U.S. Pat. No. 4,374,209, issued to Rowlands.

Another preferred class of polyols are "copolymer polyols", which are base polyols containing stably dispersed polymers such as acrylonitrile-styrene copolymers. Production of these copolymer polyols can be from reaction mixtures comprising a variety of other materials, including, for example, catalysts such as azobisisobutyronitrile; copolymer polyol stabilizers; and chain transfer agents such as isopropanol.

The formulations of the present invention can contain minor amounts of such base polyols. Preferably, base polyols will provide from about 0 to about 50 percent, more preferably from about 0 to about 40 percent and most preferably from about 0 to about 25 percent of the active hydrogens of the formulations of the present invention.

Another embodiment of the present invention is a polyurethane formulation including a polyisocyanate. The polyisocyanates of the present invention can be selected from organic polyisocyanates, modified organic polyisocyanates, organic polyisocyanate-based prepolymers, and mixtures thereof. These can include aliphatic and cycloaliphatic isocyanates, but aromatic and especially multifunctional aromatic isocyanates are preferred. Preferred are 2,4- and 2,6-toluenediisocyanate and the corresponding isomeric mixtures; 4,4'-, 2,4'- and 2,2'-diphenylmethanediisocyanate and the corresponding isomeric mixtures; mixtures of 4,4'-, 2,4'- and 2,2'-diphenylmethanediisocyanates and polyphenyl polymethylene polyisocyanates PMDI; and mixtures of PMDI and toluene diisocyanates. Also useful for preparing the polyurethanes of the present invention are aliphatic and cycloaliphatic isocyanate compounds such as 1,6-hexamethylenediisocyanate; 1-isocyanato-3,5,5-trimethyl-1-3-isocyanatomethyl-cyclohexane; 2,4- and 2,6-hexahydrotoluenediisocyanate, as well as the corresponding isomeric mixtures; 4,4'-, 2,2'- and 2,4'-dicyclohexylmethanediisocyanate, as well as the corresponding isomeric mixtures.

Also advantageously used for the polyisocyanate component are the so-called modified multifunctional isocyanates, i.e., products which are obtained through chemical reactions of the above diisocyanates and/or polyisocyanates. Exemplary are polyisocyanates containing esters, ureas, biurets, allophanates and preferably carbodiimides and/or uretonimines; isocyanurate and/or urethane group containing diisocyanates or polyisocyanates. Liquid polyisocyanates containing carbodiimide groups, uretonimine groups and/or isocyanurate rings, having isocyanate groups (NCO) contents of from 10 to 40 weight percent, more preferably from 20 to 35 weight percent, can also be used. These include, for example, polyisocyanates based on 4,4'-, 2,4'- and/or 2,2'-diphenylmethane diisocyanate and the corresponding isomeric mixtures, 2,4- and/or 2,6-toluenediisocyanate and the corresponding isomeric mixtures, 4,4'-, 2,4'- and 2,2'-diphenylmethanediisocyanate and the corresponding isomeric mixtures; mixtures of diphenylmethane diisocyanates and PMDI and mixtures of toluenediisocyanates and PMDI and/or diphenylmethane diisocyanates.

Suitable also are prepolymers having NCO contents of from 5 to 40 weight percent, more preferably from 15 to 30 weight percent. These prepolymers are prepared by reaction of the di- and/or poly-isocyanates with materials including lower molecular weight diols, triols, but also they can be prepared with multivalent active hydrogen compounds such as di- and tri-amines and di- and tri-thiols. Individual examples are aromatic polyisocyanates containing urethane groups, preferably having NCO contents of from about 5 to about 40 weight percent, more preferably about 20 to 35 weight percent, obtained by reaction of diisocyanates and/or polyisocyanates with, for example, lower molecular weight diols, triols, oxyalkylene glycols, dioxyalkylene glycols or polyoxyalkylene glycols having molecular weights up to about 800. These polyols can be employed individually or in mixtures as di- and/or polyoxyalkylene glycols. For example, diethylene glycols, dipropylene glycols, polyoxyethylene glycols, polyoxypropylene glycols and polyoxypropylenepolyoxyethylene glycols can be used.

Particularly useful in the present invention are: (i) polyisocyanates having an NCO content of from 8 to 40 weight percent containing carbodiimide groups and/or urethane groups, from 4,4'-diphenylmethane diisocyanate or a mixture of 4,4'- and 2,4'-diphenylmethane diisocyanates; (ii) prepolymers containing NCO groups, having an NCO content of from 20 to 35 weight percent, based on the weight of the prepolymer, prepared by the reaction of polyoxy-alkylene polyols, having a functionality of preferably from 2 to 4 and a molecular weight of from about 800 to about 15,000 with 4,4'-diphenylmethane diisocyanate or with a mixture of 4,4'- and 2,4'-diphenylmethane diisocyanates and mixtures of (i) and (ii); and (iii) 2,4- and 2,6-toluene-diisocyanate and the corresponding isomeric mixtures. PMDI in any of its forms can also be used and is preferred. In this case it preferably has an equivalent weight between about 125 and about 300, more preferably from about 130 to about 175, and an average functionality of greater than about 2. More preferred is an average functionality of from about 2.5 to about 3.5. The viscosity of the polyisocyanate component is preferably from about 25 to about 5,000 centipoise (cps) (0.025 to about 5 Pa.s), but values from about 100 to about 1,000 cps at 25° C. (0.1 to 1 Pa.s) are preferred for ease of processing. Similar viscosities are preferred where alternative polyisocyanate components are selected.

Polyurethane formulations usually consist of two components. An isocyanate component (hereinafter A side) and a isocyanate reactive component (hereinafter B side). The formulations of the present invention can also include another component including additives, catalysts and the like (hereinafter C side). Often the additives and catalysts are included in the B side.

Additives which can be used with the formulations of the present invention include any known to be useful by one of ordinary skill in the art of preparing polyurethanes to be useful. For example, additives such as fillers, antioxidants, flame retardants can be used with the present invention. Other additive useful include, but are not limited to: pigments, impact modifiers, ordorants, and the like.

The formulations of the present invention advantageously include a carbon dioxide blowing agent. However, any blowing agent or mixture thereof as well as a carbon dioxide blowing agent is suitable for use in the practice of the invention. Suitable blowing agents include inorganic blowing agents such as water, organic blowing agents which are volatile at reaction temperatures and dissolved inert gases. Suitable organic blowing agents include acetone; ethyl acetate; methanol; ethanol; halogen-substituted alkanes such as methylene chloride, chloroform, ethylidene chloride, vinylidene chloride, monofluorotri-chloromethane, chlorodifluoromethane, dichlorodi-fluoromethane and the like; butane; hexane; heptane; pentane; diethyl ether; and the like. Gases inert to the starting components such as nitrogen, air, carbon dioxide and the like are also useful blowing agents. Compounds, such as azides, which decompose at suitable temperatures to produce gases such as nitrogen are also useful. Preferred blowing agents are compounds which boil between about −50° and 100° C., more preferably between about 0° and 50° C.

The amount of blowing agent employed is not critical to the invention, but is preferably sufficient to foam the reaction mixture. The amount will vary with factors such as the density desired in a foamed product.

Water is a useful blowing agent for use in the practice of the invention. In addition to generating carbon dioxide gas for foaming, water reacts quickly with polyisocyanate components, thus contributing to early polymer strength needed for gas retention. Generally, when water is used, it is present in proportions of from about 1.5 to about 8 weight percent of water based on total weight of active hydrogen components.

The formulations of the present invention can include an isocyanurate and/or a urethane catalyst. The polyurethane catalyst is preferably incorporated in the formulation in an amount suitable to increase the rate of reaction between the isocyanate groups of the composition of the present invention and a hydroxyl-reacting species. Although a wide variety of materials is known to be useful for this purpose, the most widely used and preferred catalysts are the tertiary amine catalysts and the organotin catalysts.

Examples of the tertiary amine catalysts include, for example, triethylenediamine, N-methyl morpholine, N-ethyl morpholine, diethyl ethanolamine, N-coco morpholine, 1-methyl-4-dimethylaminoethyl piperazine, 3-methoxy-N-dimethylpropylamine, N,N-diethyl-3-diethyl aminopropylamine, dimethylbenzyl amine and the like. Tertiary amine catalysts are advantageously employed in an amount from about 0.01 to about 2 percent by weight of the polyol formulation.

Examples of organotin catalysts include dimethyltin dilaurate, dibutyltin dilaurate, dioctyltin dilaurate, stannous octoate and the like. Other examples of effective catalysts include those taught in, for example, U.S. Pat. No. 2,846,408. Preferably the organotin catalyst is employed in an amount from about 0.001 to about 0.5 percent by weight of the polyol formulation.

Suitable catalysts for use with the present invention which catalyze the formation of isocyanurates are such as those mentioned in Saunders and Frisch, *Polyurethanes, Chemistry and Technology;* in 1 *High Polymers* Vol. XVI, pp. 94–97 (1962). Such catalysts are referred to herein as trimerization catalysts. Examples of these catalysts include aliphatic and aromatic tertiary amine compounds, organometallic compounds, alkali metal salts of carboxylic acids, phenols and symmetrical triazine derivatives. Preferred catalysts are potassium salts of carboxylic acids such as potassium octoate and tertiary amines such as, for instance, 2,4,6-tris(dimethyl aminomethyl) phenol.

The following examples are provided to illustrate the present invention. The examples are not intended to limit the scope of the present invention and they should not be so interpreted. Amounts are in weight parts or weight percentages unless otherwise indicated.

EXAMPLE 1

AROMATIC POLYETHER POLYOL SYNTHESIS

Step 1: Preparation of Initiator 1,164 grams of diethanolamine are charged into a 4 liter flask equipped with a stirrer, thermocouple, condenser and nitrogen pad. The flask is heated to 100° C. and 1836 grams of cresyl glycidyl ether are gradually added to the flask with stirring over 90 minutes. The reaction product is analyzed and shown to have an OH percent of 19.9 an a viscosity of 64,000 cps (64 Pa.s) at 25° C.

Step 2: Alkoxylation 4,852 grams of the reaction product of Step 1 and 21.8 grams of dimethyl cyclohexyl amine are charged into a 5 gallon (18.9 liter)pressure vessel. The vessel is heated to 95° C. and 1,175 grams of ethylene oxide are added gradually over 3 hours at a pressure of 50-60 psi (345-414 mPa). The vessel is heated for four additional hours and the resulting product is then stripped at 120° C. for 4 hours. The product is analyzed and shown to have an OH percent of 15.9 and a viscosity of 6,500 cps (6.5 Pa.s) at 25° C.

EXAMPLE 2

THIN FILM PERMEABILITY MEASUREMENTS

Thin films are prepared with the reaction products of Example 1, Step 1 and Step 2, a material similar to that of Step 2 except that propylene oxide is used instead of ethylene oxide and a control polyol by admixing the material to be tested and polymethylene polyphenyl polyisocyanate (isocyanate equivalent weight of 134) at the indicated isocyanate index and then pouring the admixture onto a teflon plate heated to 180° C. The admixture is then inserted into a press with a 5 mil (0.13 mm) spacer and pressure applied for at least 2 hours. Film thickness was determined to be from 5 to 10 mil (0.13 to 0.26 mm) for each film.

Oxygen permeabilities through film samples of polymer are determined using an OXTRAN 10/50A* Permeability Analyzer (*OXTRAN 10/50A is a trade designation of Modern Controls, Inc.). The measurements are performed at 25° C. (thermostated with a constant temperature bath and circulator) using pure oxygen under either humid or dry conditions. The permeability (transmission rate) is obtained by placing the film across the test cell while purging oxygen onto the upstream side of this barrier. Permeability was determined after steady-state conditions are achieved, wherein the polymer is saturated with gas (under the test conditions) and the transmission rate at a stable value. The films are subjected to at least three days under the experimental conditions in order to ensure the reading of a steady state transmission rate. A relative humidity of 50 percent to 75 percent ("wet") is obtained in the permeation cell by sending the gases through bubblers containing distilled water. An environment of approximately 0% relative humidity ("dry") is maintained by routing the dried gases directly to the testing cell. Carbon dioxide permeability through the film samples was measured using a PERMATRAN C-200* (*PERMATRAN C-200 is a trade designation of Modern Controls, Inc.) computer controlled instrument. The films are tested at 25° C. under "dry" conditions using pure carbon dioxide.

The precision of the measurement of gas permeability through films is assessed by repeatedly measuring the transmission rate of a film standard throughout the course of the experiments. The reproducibility of the transmission rate measurement is approximately ±1 percent. The accuracy of the permeability values is primarily influenced by the accuracy in the measurement of film thickness. Since small variations in film thickness (±0.4 mil) occur over a film's area, the accuracy of the permeability determination is estimated to be about ±6 percent.

The permeability rates for the indicated films are displayed below in Table 1.

TABLE 1

|  | index | $O_2$ wet | $O_2$ dry | $CO_2$ dry |
|---|---|---|---|---|
| DEOA[1] | 105 | 6.3 | 8.5 | 44.7 |
| DEOA[1] | 67 | 2.0 | 2.6 | 7.0 |
| DEOA-PO[2] | 105 | 10.3 | 10.8 | 56.2 |
| DEOA-PO[2] | 67 | 2.6 | 2.9 | 14.3 |
| DEOA-EO[3] | 105 | 2.4 | 2.6 | 12.4 |
| DEOA-EO[3] | 67 | 2.0 | 2.4 | 10.4 |
| CONTROL[4]* | 105 | 10.0 | 13.3 | 80.6 |

* Not an example of the present invention.
Units are ml*mil/100 in$^2$ * day * Atm
1. DEOA: reaction product of cresyl glycidyl ether and diethanol amine.
2. DEOA-PO: reaction product of cresyl glycidyl ether and diethanol amine capped with propylene oxide.
3. DEOA-EO: reaction product of cresyl glycidyl ether and diethanol amine capped with ethylene oxide.
4. VORANOL 490**. A control polyol prepared using a sucrose and glycerine initiator having an equivalent weight of about 115 and a nominal functionality of 4
**(VORNAL 490 is a trade designation of The Dow Chemical Company).

EXAMPLE 3

HIGH INDEX FOAM EXAMPLE

Polyurethane foams are prepared by admixing formulations displayed below in Table 2 using a drill press equipped with a Cowles mixing blade at 1,000 rpm for 10 seconds at ambient temperature. The foaming admixture is then poured into a 14"×14"×14" (35.6 cm×35.6 cm×35.6 cm) box. The foams are then tested and the results are displayed below in Table 3

COMPARATIVE EXAMPLE 4

A foam is prepared and tested substantially identically to Example 3 except a conventional polyol is used. The formulation is displayed below in Table 2 and the test results are displayed below in Table 3.

TABLE 2

| INGREDIENT | EXAMPLE 3 | COMPARATIVE EXAMPLE 4* |
|---|---|---|
| DEOA-EO[1] | 100 |  |
| VORANOL 490[2,4] |  | 100 |
| Water | 4.05 | 4.05 |
| DC 5367[3,B] | 4.04 | 4.04 |
| PC-5[4,C] | 0.35 | 0.35 |
| HEXCEM 977[5,D] | 8.44 | 8.44 |
| HCFC-141B[6,E] | 37.1 | 37.1 |
| PAPI 580[7,A] | 510.8 | 510.8 |

*Not an example of the present invention.
1. DEOA-EO: reaction product of cresyl glycidyl ether and diethanol amine, capped with ethylene oxide.
2. VORANOL 490 is a control polyol prepared using a sucrose and glycerine initiator having an equivalent weight of about 115 and a nominal functionality of 4.
3. DC 5367 is a silicone surfactant.
4. PC-5 (POLYCAT 5) is a tri-tertiary amine catalyst.
5. HEXCEM 977 is a potassium octoate catalyst.
6. HCFC-141B is a hydrochlorofluorocarbon blowing agent.
7. PAPI 580 is a polymethylene polyphenyl polyisocyanate having an isocyanate equivalent weight of 138.
A. VORANOL 490 and PAPI 580 are trade designations of The Dow Chemical Company.
B. DC 5367 is a trade designations of Air Products and Chemicals Inc.

TABLE 3

| PROPERTY | EXAMPLE 3 | COMPARATIVE EXAMPLE 4* |
|---|---|---|
| Density[1] (pcf/kg/m$^3$) | 2.10/33.64 | 2.15/34.43 |
| Abrasion[2] (% loss) | 47.2 | 51.4 |
| Compressive X | 14.1/97.2 | 14.3/98.6 |
| Strength[3] Y | 48.2/332.3 | 36.2/249.6 |
| (psi/mPa) Z | 19.9/137.2 | 18.5/127.6 |
| Dimensional Cold | −2.3 | −0.38 |
| Stability[4] Hot | −0.54 | 1.1 |
| (% change) Humid | 0.75 | 1.05 |
| % Closed Cell[5] | 94.8 | 94.1 |
| K-factor[6] Days |  |  |

TABLE 3-continued

| PROPERTY | EXAMPLE 3 | COMPARATIVE EXAMPLE 4* |
|---|---|---|
| 0 | 0.145 | 0.153 |
| 7 | 0.152 | 0.171 |
| 14 | 0.152 | 0.182 |
| 21 | 0.154 | 0.189 |
| 28 | 0.156 | 0.196 |
| 60 | 0.170 | 0.209 |

\* Not an example of the present invention.
1. ASTM D-1622-83
2. ASTM C-421-83
3. ASTM D-1621-73
4. ASTM D-2126-75
5. ASTM D-2856-70
6. ASTM C-518-85

EXAMPLE 5

ON INDEX FOAM EXAMPLE

A polyurethane foam is prepared and tested substantially identically to Example 3 except that the formulation displayed below in Table 4 is used. Test results are displayed below in Table 5.

COMPARATIVE EXAMPLE 6

A polyurethane foam is prepared and tested substantially identically to Example 5 except that a conventional polyol is used. The formulation is displayed below in Table 4. Test results are displayed below in Table 5.

TABLE 4

| INGREDIENT | EXAMPLE 5 | COMPARATIVE EXAMPLE 6* |
|---|---|---|
| DEOA-EO[1] | 75 | |
| VORANOL 490[2,A] | | 75 |
| PS 3152[3,B] | 25 | 25 |
| Water | 0.48 | 0.46 |
| DC 5357[4,C] | 2.6 | 2.4 |
| PC-5[5,D] | 0.48 | 0.92 |
| PC-8[6,D] | 0.36 | 0.67 |
| TMR-2[7,E] | 0.26 | 0.48 |
| T-12[8,F] | 0.026 | 0.012 |
| HCFC-141B[9,G] | 22.6 | 21.4 |
| PAPI 27[10] | 125.6 | 113.2 |

*Not an example of the present invention.
1. DEOA-EO: reaction product of cresyl glycidyl ether and diethanol amine, capped with ethylene oxide.
2. VORANOL 490 is a control polyol prepared using a sucrose and glycerine initiator having an equivalent weight of about 115 and a nominal functionality of 4.
3. PS 3152 is a 180 equivalent weight polyol having a functionality of 2.
4. DC 5357 is a silicone surfactant.
5. PC-5 (POLYCAT 5) is a tri-tertiary amine catalyst.
6. PC-8 (POLYCAT 8) is a tertiary amine catalyst.
7. TMR-2 is a quaternary ammonium salt catalyst.
9. T-12 is a dibutyl tin dilaurate catalyst
10. HCFC-141B is a hydrochlorofluorocarbon blowing agent.
11. PAPI 27 is a polymethylene polyphenyl polyisocyanate having an isocyanate equivalent weight of 135.
A. VORANOL 490 and PAPI 27 are trade designations of The Dow Chemical Company.
B. PS 3152 is a trade designation of Stepan Chemical Company.
C. DC 5367 is a trade designations of Air Products and Chemicals Inc.
D. POLYCAT 5 and POLYCAT 8 are trade designations of Air Products and Chemicals Inc.
E. TMR-2 is a trade designation of Air Products and Chemicals Inc.
F. T-12 is a trade designation of Air Products and Chemicals Inc.
G. HCFC-141B is a trade designation of Atochem.

TABLE 5

| PROPERTY | EXAMPLE 3 | COMPARATIVE EXAMPLE 6* |
|---|---|---|
| Density[1] (pcf/kg/m$^3$) | 2.05/32.84 | 2.12/33.63 |
| Abrasion[2] (% loss) | 0.53 | 0.58 |
| Compressive X Strength[3] Y | 9.3/64.12 28.4/195.81 | 14.9/102.73 46.1/317.85 |
| (psi/mPa) Z | 8.8/60.67 | 19.9/137.2 |
| Dimensional Cold | −12.9 | 0.12 |
| Stability[4] Hot | 78.2 | 12.2 |
| (% change) Humid | 45.2 | 16.6 |
| % Closed Cell[5] | 92.8 | 93.9 |
| K-factor[6] Days | | |
| 0 | 0.129 | 0.134 |
| 7 | 0.131 | 0.138 |
| 14 | 0.131 | 0.141 |
| 21 | 0.132 | 0.144 |
| 28 | 0.134 | 0.147 |
| 60 | 0.138 | 0.157 |

\* Not an example of the present invention.
1. ASTM D-1622-83
2. ASTM C-421-83
3. ASTM D-1621-73
4. ASTM D-2126-75
5. ASTM D-2856-70
6. ASTM C-518-85

EXAMPLE 7

POLYESTER POLYOL SYNTHESIS 55.94 grams of sorbitol, 54.10 grams of ethylene carbonate and 0.11 grams of potassium carbonate are charged into a 500 ml round bottom flask equipped with a thermometer, a stirrer, condenser and a nitrogen pad. The flask is heated to 150° C. for 8 hours at which time an infrared spectrum shows complete disappearance of the ethylene carbonate peak at 1795cm$^{-1}$. Next, 113.73 grams of phthalic anhydride, 130.33 grams of diethylene glycol and 0.30 grams of dibutyl tin dilaurate are charged to the flask and the flask is heated to: 150° C. for one hour, 180° C. for one hour, 200° C. for one hour, 220° C. for one hour and 240° C. for 2 hours. During the final hour, a vacuum is applied to remove volatiles. The resulting 295.2 grams of product has a percent OH of 14.84, viscosity of 2180 cps (2.18 Pa.s) at 25° C. and an acid value of 1.3.

EXAMPLE 8

POLYESTER POLYOL SYNTHESIS 53.8 grams of sorbitol, 52.0 grams of ethylene carbonate and 0.36 grams of manganese acetate are charged into a 500 ml round bottom flask equipped with a thermometer, a stirrer, condenser and a nitrogen pad. The flask is heated to 180° C. for 8 hours at which time an infrared spectrum shows complete disappearance of the ethylene carbonate peak at 1795cm$^{-1}$. Next, 143.3 grams of dimethyl terephthalate and 125.3 grams of diethylene glycol are charged to the flask and the flask is heated to: 170° C. for two hours, 180° C. for one hour, a vacuum applied and heating continued at 180° C. for one hour, 190° C. for one hour 200° C. for one hour and 210° C. for 2 hours. The resulting 302.1 grams of product has a percent OH of 14.79 and a viscosity of 2730 cps (2.73 Pa.s) at 25° C.

COMPARATIVE EXAMPLE 9

55.94 grams of sorbitol, 113.73 grams of phthalic anhydride, 130.33 grams of diethylene glycol and 0.30 grams of dibutyl tin dilaurate are charged into a 500 ml round bottom flask equipped with a thermometer, a stirrer, condenser, and a nitrogen pad. The flask is heated to: 150° C. for one hour, 180° C. for one hour, 200° C. for one hour, 220° C. for one hour and 240° C. for 2 hours. During the final hour, a vacuum is applied to remove volatiles. The resulting 274.7 grams of product has a percent OH of 11.2, viscosity of 28,080 cps (28.08 Pa.s) at 25° C. and an acid value of 13.7.

COMPARATIVE EXAMPLE 10

A sorbitol-ethylene oxide polyol is prepared by reacting 571 grams of sorbitol with 830.0 grams of ethylene oxide in the presence of 15.7 grams KOH catalyst. The resultant polyol is a viscous semisolid with percent OH of 24.0.

The polyester polyol is prepared and tested substantially identically to Comparative Example 9 except that 104.59 grams of the sorbitol-ethylene oxide polyol from above, 91.06 grams of phthalic anhydride, 104.35 grams of diethylene glycol and 0.30 grams of dibutyl tin dilaurate are used. The resulting 280.1 grams of product has a percent OH of 10.68, a viscosity of 24,400 cps (24.40 Pa.s) at 25° C. and an acid value of 14.8.

COMPARATIVE EXAMPLE 11

A polyester polyol is prepared and tested substantially identically to Comparative Example 9 except that 123.33 grams of phthalic anhydride, 176.67 grams of diethylene glycol, and 0.30 grams of dibutyl tin dilaurate are used. The resulting 283.0 grams of product has a percent OH of 9.26, a viscosity of 2,560 cps (2.56 Pa.s) at 25° C. and an acid value of 1.1.

EXAMPLE 12

THIN FILM PERMEABILITY MEASUREMENTS

Thin films are prepared and permeability determined substantially identically to Example 2 above. Results are displayed below in Table 6.

TABLE 6

|  | index | $O_2$ wet | $O_2$ dry | $CO_2$ dry |
|---|---|---|---|---|
| Ex. 7 | 105 | 1.7 | 2.1 | 11.2 |
| Ex. 7 | 67 | 0.6 | 0.65 | 6.7 |
| Ex. 9* | 105 | 1.4 | 1.6 | no data |
| Ex. 9* | 71 | 0.84 | 0.65 | 8.1 |
| Ex. 10* | 80 | 1.1 | 1.2 | no data |
| Ex. 11* | 105 | 0.97 | 1.2 | 6.0 |
| Ex. 11* | 80 | 2.8 | 1.6 | 10.6 |
| G-2EO** | 105 | 4.6 | 6.5 | 39.2 |
| G-2EO** | 67 | 1.2 | 2.4 | 10.3 |

* Not an example of the present invention.
Units are ml*mil/100 in² * day * Atm
** G-2EO is a polyether polyol prepared with 2 moles of ethylene oxide and 1 mole of glycerine with a KOH catalyst.

EXAMPLES 13 and 14

FOAM EXAMPLES

Foams are prepared and tested substantially identically to Example 3 above except that formulations displayed below in Table 7 are used. Test results are displayed below in Table 8.

TABLE 7

| INGREDIENT | EXAMPLE 13 | EXAMPLE 14 |
|---|---|---|
| Example 7[1] | 75 | 75 |
| G-2EO[2] | 25 | 25 |
| Water | 0.52 | 0.50 |
| DC 5357[3,4] | 3.5 | 3.0 |
| PC-5[4B] | 0.7 | 0.7 |
| PC-8[5B] | 0.49 | 0.50 |
| TMR-2[6C] | 0.35 | 0.40 |
| T-12[7D] | 0.014 | 0.012 |
| HCFC-141B[8E] | 24.4 | 21.3 |

TABLE 7-continued

| INGREDIENT | EXAMPLE 13 | EXAMPLE 14 |
|---|---|---|
| PAPI 27[9F] | 143.7 | 161.1 |

TABLE 8

| PROPERTY | EXAMPLE 13 | EXAMPLE 14 |
|---|---|---|
| Density[1] (pcf/kg/m³) | 1.69/27.07 | 1.71/27.39 |
| Abrasion[2] (% loss) | 0.2 | 0.2 |
| Compressive X | 10.5/72.39 | 8.8/60.67 |
| Strength[3] Y (psi/mPa) Z | 38.1/262.69 | 43.4/299.23 |
|  | 7.3/50.33 | 12.0/82.73 |
| Dimensional Cold | −55.0 | −0.26 |
| Stability[4] Hot | 23.0 | 4.4 |
| (% change) Humid | 53.0 | 12.9 |
| % Closed Cell[5] | 94.2 | 88.3 |
| K-factor[6] Days |  |  |
| 0 | 0.125 | 0.130 |
| 7 | 0.127 | — |
| 8 | — | 0.133 |
| 14 | 0.128 | 0.133 |
| 21 | 0.129 | — |
| 22 | — | 0.133 |
| 28 | 0.131 | 0.133 |
| 62 | 0.131 | 0.136 |

1. ASTM D-162283
2. ASTM C-421-83
3. ASTM D-1621-73
4. ASTM D-2126-75
5. ASTM D-2856-70
6. ASTM C-518-85

What is claimed is:

1. A polyester polyol useful for preparing polyurethane foams having improved retention of insulative properties comprising the product of
   (1) admixing ethylene carbonate and one or more hydroxyl functional compounds under reaction conditions sufficient to react the ethylene carbonate and the hydroxyl functional compounds to produce a polyol precursor, and
   (2) admixing the polyol precursor with diethylene glycol and an anhydride, a dicarboxylic acid, a tricarboxylic acid or mixtures thereof, optionally in the presence of a catalyst, under reaction conditions sufficient to prepare a polyester polyol, wherein the hydroxyl functional compounds are selected from glycerine, trimethylpropane, sugars and sugar derivatives.

2. The polyol of claim 1 wherein the hydroxyl functional compounds have a minimum nominal functionality of 2 and a maximum nominal functionality of 12 and have from 2 to 24 carbon atoms.

3. The polyol of claim 2 wherein the sugar and sugar derivatives are selected from the group consisting of pentaerythritol, xylitol, arabitol, sorbitol, mannitol, fructose, sucrose, α-methyl glucoside, and β-methyl glucoside.

4. A method of preparing a polyester polyol useful for preparing polyurethane foams having improved retention of insulative properties comprising the steps of
   (1) admixing ethylene carbonate and one or more hydroxyl functional compounds under reaction conditions sufficient to react the ethylene carbonate and the hydroxyl functional compounds to produce a polyol precursor, and
   (2) admixing the polyol precursor with diethylene glycol and an anhydride, a dicarboxylic acid, a tricarboxylic acid or mixtures thereof, optionally in the presence of a catalyst, under reaction conditions sufficient to prepare a polyester polyol, wherein the hydroxyl functional compounds are selected from glycerine, trimethylpropane, sugars and sugar derivatives.

* * * * *